(12) United States Patent
Winegarden et al.

(10) Patent No.: US 6,902,702 B1
(45) Date of Patent: Jun. 7, 2005

(54) DEVICES AND METHODS FOR PRODUCING MICROARRAYS OF BIOLOGICAL SAMPLES

(75) Inventors: Neil A. Winegarden, Burlington (CA); James B. McNeil, Newmarket (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 09/723,400

(22) Filed: Nov. 27, 2000

Related U.S. Application Data (60) Provisional application No. 60/225,783, filed on Aug. 17, 2000.

(30) Foreign Application Priority Data

Aug. 16, 2000 (CA) ............................................. 2316045

(51) Int. Cl.[7] .................................................. G01N 1/10
(52) U.S. Cl. ......................... 422/100; 422/99; 436/180; 73/864.22
(58) Field of Search .......................... 422/100, 99, 103, 422/102, 104, 129–131; 73/863.33, 864.22; 141/236, 244; 436/180; 269/21; 134/21, 43, 44, 171

(56) References Cited

U.S. PATENT DOCUMENTS

| | | | | |
|---|---|---|---|---|
| 2,691,381 A | * | 10/1954 | Strunck et al. | 134/152 |
| 2,708,943 A | * | 5/1955 | Watson et al. | 134/62 |
| 3,836,329 A | | 9/1974 | Jordan | |
| 4,256,152 A | * | 3/1981 | Belanger et al. | 141/70 |
| 4,439,526 A | * | 3/1984 | Columbus | 204/409 |
| 4,685,480 A | | 8/1987 | Eck | |
| 4,753,775 A | * | 6/1988 | Ebersole et al. | 422/81 |
| 4,810,471 A | | 3/1989 | Wachob et al. | |
| 4,832,842 A | * | 5/1989 | Limb | 210/249 |
| 5,009,241 A | * | 4/1991 | Nishizawa | 134/102.1 |

(Continued)

FOREIGN PATENT DOCUMENTS

| | | |
|---|---|---|
| CA | 2276462 | 7/1998 |
| CA | 2349382 | 5/1999 |
| CA | 2348532 | 5/2000 |
| CA | 2356946 | 7/2000 |
| CA | 2340807 | 10/2001 |
| WO | WO 97/40383 | * 10/1997 |
| WO | WO 98/04358 | * 2/1998 |
| WO | WO 99/01261 | 1/1999 |

OTHER PUBLICATIONS

TeleChem International, Inc. "ChipMaker 3" "ChipMaker 2".*

(Continued)

*Primary Examiner*—Jill Warden
*Assistant Examiner*—Jyoti Nagpaul
(74) *Attorney, Agent, or Firm*—Blackwell Sanders Peper Martin LLP (57) ABSTRACT

The present invention is directed to systems and methods for producing microarrays of biological samples using an improved slide platform, vacuum manifold, and variable pin contact velocity. Slides onto which spotting pins produce the microarray of biological samples are secured on a flat slide platform using magnetic unit bars. The vacuum manifold effects optimal cleaning of the spotting pins by inducing increased air flow and turbulence. By reducing the velocity of the spotting pins before or after contact with the blot pad or the microarray slide, the morphology of biological samples deposited may be kept uniform. Similarly, low impact and separating velocities while acquiring biological materials prevent the pins from being overloaded with solution on the outside of the pin and causing sample wastage and non-uniform spotting.

25 Claims, 6 Drawing Sheets

U.S. PATENT DOCUMENTS

| | | | |
|---|---|---|---|
| 5,055,263 A | | 10/1991 | Meltzer |
| 5,138,868 A | | 8/1992 | Long |
| 5,306,510 A | | 4/1994 | Meltzer |
| 5,445,934 A | | 8/1995 | Fodor et al. |
| 5,803,987 A | * | 9/1998 | DeWitt et al. ............. 134/25.4 |
| 5,827,246 A | | 10/1998 | Bowen |
| 5,866,825 A | * | 2/1999 | Moore et al. ............ 73/864.22 |
| 5,879,944 A | | 3/1999 | Komatsu |
| 5,935,859 A | * | 8/1999 | Elliott et al. ................ 422/100 |
| 5,948,358 A | | 9/1999 | Saito |
| 5,976,470 A | * | 11/1999 | Maiefski et al. ............ 222/485 |
| 5,985,214 A | | 11/1999 | Stylli et al. |
| 6,054,100 A | * | 4/2000 | Stanchfield et al. ........ 422/102 |
| 6,084,373 A | | 7/2000 | Goldberg et al. |
| 6,086,825 A | * | 7/2000 | Sundberg et al. .......... 422/100 |
| 6,133,045 A | | 10/2000 | Johnson et al. |
| 6,170,494 B1 | * | 1/2001 | Marinaro et al. ........ 134/22.18 |
| 6,240,984 B1 | * | 6/2001 | Fawcett et al. ............. 141/129 |
| 6,245,297 B1 | * | 6/2001 | Kowallis .................... 422/100 |
| 6,255,116 B1 | * | 7/2001 | Leber et al. ................ 422/100 |
| 6,258,324 B1 | * | 7/2001 | Yiu ........................... 422/100 |
| 6,267,930 B1 | * | 7/2001 | Ruediger et al. ........... 422/100 |
| 6,274,091 B1 | * | 8/2001 | Mohan et al. .............. 422/100 |
| 6,287,872 B1 | * | 9/2001 | Schurenberg et al. ....... 422/100 |
| 6,309,891 B1 | * | 10/2001 | Shalon et al. ............... 436/180 |
| 6,326,212 B1 | * | 12/2001 | Aoki ............................. 222/1 |
| 6,347,259 B1 | | 2/2002 | Goldenberg et al. |
| 6,355,487 B2 | * | 3/2002 | Kowallis .................... 422/100 |
| 6,416,713 B1 | * | 7/2002 | Ford et al. ............... 137/519.5 |
| 6,428,752 B1 | * | 8/2002 | Montagu .................... 422/104 |
| 6,447,661 B1 | * | 9/2002 | Chow et al. ................ 204/453 |
| 6,451,188 B1 | * | 9/2002 | Sundberg et al. ........... 204/453 |
| 6,455,007 B1 | * | 9/2002 | Mansky et al. ............. 422/101 |
| 6,475,444 B1 | * | 11/2002 | Zimmermann et al. ..... 422/102 |
| 6,551,557 B1 | * | 4/2003 | Rose et al. ................. 422/100 |
| 2002/0106308 A1 | * | 8/2001 | Zweifel et al. ............. 422/100 |

OTHER PUBLICATIONS

N. Winegarden. "Calibrating the SDDC–2 Microarray Robot From ESI." Version 1.1—Mar. 26th, 2000, Ontario Cancer Institute, University Health Network.

N. Winegarden. "Microarray Technology Development." The Toronto Gene Chip Consortium, Princess Margaret Hospital, Ontario Cancer Institute, May 27, 1999.

N. Winegarden. "Microarrays: Questions and Answers." Toronto Microarray Consortium, Ontario Cancer Institute, Nov. 1999.

J. DeRisi et al. "A complete guide to building your own microarrayer." Version 2.0, Biochemistry Department, Stanford University, University of California, San Francisco, 1998–1999.

J. DeRisi et al. "A complete guide to building your own microarrayer." Version 1.1, Biochemistry Department, Stanford University, 1998.

J. DeRisi et al. "A complete guide to building your own microarrayer." Version 1.0, Biochemistry Department, Stanford University, 1998.

Office of the Vice President, Reseach, University Health Network. Net Results. "Mircoarrays—The Future of Genetics." Fall 1999 issue. Dec. 1999.

Engineering Services Inc. Webpages. Jan. 28, 1999.

Engineering Services Inc. SDDC–2: DNA Arrraying Cell. Undated.

Remarks on the occasion of Minister of Energy, Science and Technology launch of ORDCF grants at OCI/UHN with draft press release. Dec. 9, 1999.

Andrew Goldenberg "DNA Micro–Arraying Robot." Absract was presented at Methods and Models in Automation and Robotics (Europe 2000) and 8th Institute of Electrical and Electronics Engineers, Inc. Mediterranean Conference on Control and Automation, Jul. 17–19, 2000, Greece.

PowerPoint Presentation entitled: "Microarrays: Beyond the Blackmagic." Toronto Gene Chip Consortium, Jun. 14, 2000.

Press Release Entitled "Virtek Vision International Inc. Acquires Biotechnology Business of Engineering Services Inc." Jul. 26, 2000.

Product Literature from Eurogentec (SDDC–2 European distributor). A new spot in the array sky. Undated. Believed to have been disclosed in mid–2000 in Europe.

Virtek Chipwriter™ SDDC User's Guide (Version 2.5). Dec. 2000.

Virtek Chipwriter™ SDDC User Interface Guide (Version 2.5). Dec. 2000.

Virtek Chipwriter™ SDDC Robot Language Manual (Version 2.5). Dec. 2000.

Engineering Services Inc. (ESI). SDDC–2 User's Guide (Version 2.4). May 2000.

Engineering Services Inc. (ESI). SDDC–2 User Interface Guide (Version 2.4). Jun. 2000.

Engineering Services Inc. (ESI). SDDC/C200 Robot Language Manual (Version 2.4). Jun. 2000.

* cited by examiner

DEVICES AND METHODS FOR PRODUCING MICROARRAYS OF BIOLOGICAL SAMPLES

CROSS REFERENCE TO RELATED APPLICATION

This application is based on and claims priority of Canadian Patent Application Serial No. 2,316,045 filed Aug. 16, 2000 and U.S. Provisional Patent Application Ser. No. 60/225,783 of Winegarden et al for DEVICES AND METHODS FOR PRODUCING MICROARRAYS OF BIOLOGICAL SAMPLES, filed Aug. 17, 2000, which is hereby incorporated by reference.

FIELD OF THE INVENTION

The invention relates to systems and methods for producing microarrays for biological investigation. In particular, this invention is directed to systems and methods for producing microarrays using improved slide platforms and vacuum manifolds, and variable pin contact velocity.

BACKGROUND OF THE INVENTION

Information about genes is critical to understanding the biological processes which underlie life: cellular communication, growth, movement, reproduction, and control. Once obtained, the structural and functional features of the genetic sequences (polypeptides and polynucleotides) enable better diagnostics and treatment of disease and defects, whether genetic or external in origin.

Traditional gene expression research has involved manual pipetting of samples onto gels, membranes or filters, or into multiwell plates. These methodologies are extremely time consuming, laborious, low throughput and expensive (on a per gene basis).

Modern microarray technologies get around a number of the above problems by automating the spotting process using robotics which permits high density spotting of slides, also known as microarray slides, which allows thousands of gene fragments to be analyzed in a single experiment (Schena M, Shalon D, Davis R W, Brown PO. "Quantitative monitoring of gene expression patterns with a complementary DNA microarray", Science 270, 467470 (1995); Southern, E, Mir K, and Shchepinov, M, Molecular Interactions on microarrays, Nature Genet. 21, 5–9 (1999)). Each spot leaves a sample of volume in the nanoliter range, the centres of adjacent spots separated by micrometers.

Array types include oligonucleotide arrays, cDNA arrays and genomic DNA arrays. For example, one application is to identify the genes, the expression or repression of which results in the difference between a normal human cell and a mutant human cell. Cells contain thousands of genes, a few thousand in lower organisms such as yeast and over 100,000 in humans; a cDNA is made for each gene and spotted onto gene chips as part of the microarray. Another application concerns the construction of olionucleotide arrays. It is also possible for genomic DNA arrays (chromosomal DNA) to be fabricated using modern microarray technology. Arrays are also useful for DNA sequencing.

Typically, a microarrayer has a number of components including: (1) a robotic mechanism; (2) a dispenser assembly; (3) means for replenishing the spotting dispensers with the biological sample; (4) a platform to support the microarray slides during spotting; (5) means for cleaning the spotters; and (6) software to operate the robot mechanism and provide an interface with a user. Samples are typically stored in source plates. Source plate plastics may be polystyrene, polypropylene or polycarbonate. In general, plates may have 1536, 384 or 96 wells. DNA may be attached to the substrate through any suitable technique (e.g. covalent or ionic bonding). Dispensers for spotting, also known as spotting members, include pins, which in turn include solid pins, split or quill pins, pin and ring systems, capillaries, or inkjet systems. Pins include the Telechem Chipmaker 2 and the Telechem Chipmaker 3 (Stealth Pins).

Recent advances in robotics such as that disclosed by the invention in U.S. Pat. No. 6,048,373, have made possible a number of features desired in an ideal microarrayer: (1) high resolution; (2) repeatability; and (3) precision. Resolution of a system is the ability to distinguish two points as being separate; it is also the minimum distance that can be measured by an encoder. Repeatability refers to the ability of the robot to return to the same place. The difference between the position that the robot desires to occupy and the actual position occupied is the precision of the system. The density of the array is a function of the spatial resolution of the robot.

The mechanism for dispensing the biological sample typically uses pins as the part of the print head that performs the actual spotting. The preferred approach is a set of pins, either in the solid or in the split form of the pin (with a slot), typically arranged in a rectangular matrix. The biological samples are loaded into/onto the pins from the source plates. It is critical that deposition of probe biological sample, such as cDNA, yield regularly spaced spots of uniform morphology. Not all deposition pins designed to the same specifications behave in a similar manner. Each will load an amount characteristic of the pin. Consequently, the size of the first spots produced from a set of pins can be significantly variable. The greatest concern is that deposition of excessive material on the microarrays may yield overlapping spots. This will result in contamination of the material spotted on the arrays as well as the material in the probe plates. As spotting proceeds, the excess material is removed and the spots become uniform until the exhaustion of the material on the pin. There is thus a need to effectively remove the excess material prior to spotting onto the microarray slides.

It is also important to have a well-designed platform (also known as a platen) onto which the microarray slides are placed for array printing. Existing art uses a platform that had "rails" cut into it. These rails would serve to hold the slides in place in the X-axis and/or Y-axis, and allow for just enough space into which to place the slides; however in certain cases, the lack of a uniform standard on slide sizes means that certain commercially available slides would not fit into the tracks of a particular microarrayer. The rails have to be machined with great precision to hold the slides without allowing for movement. Other solutions use a set of spring loaded plastic pins, which hold the slides in place. These pins offer some compliance to allow for subtle variations in slide size (such as the difference between metric and imperial measure slides). Other units utilize a combination of machined holders for the slides with a vacuum manifold. The vacuum manifold helps hold the slides down firmly which allows the depression into which the slide sits to not be an exact fit. Again in this case slight size variations are possible allowing imperial and metric slides to be used.

These solutions do not provide for a great deal of flexibility. In addition, these slide platforms/holders are difficult to load, which causes the operation to be time consuming and increases the risk of damage to the slides. Some of these units require such a platform/holder design because the slide platform sits on top of one of the robotic actuators. In such a case the slide platform moves during the printing process and thus the slides need to be held firmly to prevent them from shifting in place. Where the robot mechanism uses an overhead gantry system; the print head travels over the slide platform in all three axes, and the slide platform remains stationary. In such a situation, there is little movement, which will cause the slides to shift. There is thus a need for a platform/slide holder, which allows for much greater flexibility, and much greater ease of use.

In order to clean the spotting pins, a vacuum or forced air removes liquid from the pins, usually present on the pins (and in the slot of the pins) as a result of dipping into a water bath for cleaning after spotting. Known vacuum manifolds are comprised of a chamber containing a series of holes (as many as there are pins for the print head) into which the pins fit. The tips of pins are generally placed into the holes, either at the opening of the hole, or completely into the vacuum chamber. These solutions are not sufficient for optimal cleaning of the pins. There is a need for a vacuum manifold and associated method to optimally clean the spotting pins.

SUMMARY OF THE INVENTION

The invention relates to a vacuum manifold for use in removing liquid from microarray spotting members, including:
- a plate defining a plurality of fluid flow channel members formed through the plate, each channel member defining an inlet and an outlet in fluid communication; and
- structure for coupling the plate to communicate with a source of vacuum to draw fluid from the microarray spotting members through the fluid flow channel members.

The invention also includes a microarrayer including the vacuum manifold.

Another embodiment of the invention relates to a method of removing liquid from a plurality of microarray spotting members, including applying a source of vacuum to the manifold of claim 1 and reciprocating the microarray spotting members proximate to the inlets of a manifold of the invention to create air turbulence between the spotting members and the inlets.

The invention also relates to a support device for holding microarray substrates in place during microarrayer operation, including:
- a flat platform on which substrates may be placed, the flat platform including an array surface including first, second, third and fourth peripheral edges;
- a first bar on the first peripheral edge;
- a second bar on the second peripheral edge, the second bar perpendicular to the first bar;
- a third bar on the third peripheral edge, the third bar perpendicular to the second bar and opposed to the first bar, the third bar capable of applying force to the substrates to hold them in place during microarray operation;
- a plurality of end bars perpendicular to the first and third bars and opposed to the second bar, the end bars capable of being located on the fourth peripheral edge or on the array surface spaced apart from the fourth peripheral edge, the end bars capable of applying force to the substrates to hold them in place during microarray operation.

The invention also includes a microarrayer including the support device.

The invention relates to a blotting device for blotting liquid from the exterior of microarray spotting members, including:
- a blotting surface for drawing liquid from the microarray spotting members when the microarray spotting members contact the blotting surface;
- structure for contacting the microarray spotting members with the blotting surface.

The invention includes a microarrayer including the blotting system.

The invention also includes a method of delivering liquid from a spotting member onto a microarray substrate for a microarray operation, including:
- advancing the spotting member from a first position to a second position, the spotting member spaced apart from the substrate in the first position and the spotting member engaging the substrate in the second position for delivering liquid, the spotting member advancing from the first position to the second position at pre-determined, variable velocity, the spotting member velocity reduced when the spotting member approaches the second position from the first position.
- permitting the spotting member to engage the substrate for a pre-determined period of time to allow the liquid to form a spot on the substrate suitable for microarray operation.

The invention also relates to a method of drawing liquid from a well into a spotting member for a microarray operation, including:
- advancing the spotting member from a first position to a second position, the spotting member spaced apart from the well in the first position and the spotting member proximate to the bottom of the well for drawing liquid in the second position, the spotting member advancing from the first position to the second position at pre-determined, variable velocity, the spotting member velocity reduced when the spotting member approaches the second position from the first position.
- permitting the spotting member to remain proximate to the bottom of the well for a pre-determined period of time to draw the liquid into the spotting member.

The invention also includes a substrate with a surface comprising 3000 or more groups of DNA molecules attached to the surface in discrete known regions, the 3000 or more groups of DNA molecules occupying a total area of less than 1 cm$^2$ on the substrate.

BRIEF DESCRIPTION OF THE DRAWINGS

Embodiments of the invention will be described by way of example and with reference to the drawings in which:

FIG. 5: Side view of a manifold with micro apertures. One preferably sets the robot up such that the pin tip just passes the opening of the hole at the down position (A), and is reciprocated up to a position a few hundred microns above the opening (B). Reciprocation up and down is used to increase air turbulence, increasing the cleaning efficiency.

FIG. 7(A): The slide platform is preferably ultra-flat machined aluminum platform. This platform is level so that there is less than 200 micrometers variance from one corner to another. Two guidebars are used to push the slides up against thus keeping them in place. A steel bar proximate to the aluminum platform is used to act as a magnetic surface for the end bar magnetic slide holders. An additional moveable heavy steel bar holds the slides in the other axis. (B) A full complement of slides was to use all of the magnetic holders and the heavy bar to keep the slides in place. (C) When only a partial complement of slides is used, only some of the end bars are required, and the heavy steel bar can be moved to hold the slides in place.

DETAILED DESCRIPTION OF THE INVENTION

Figure 9:
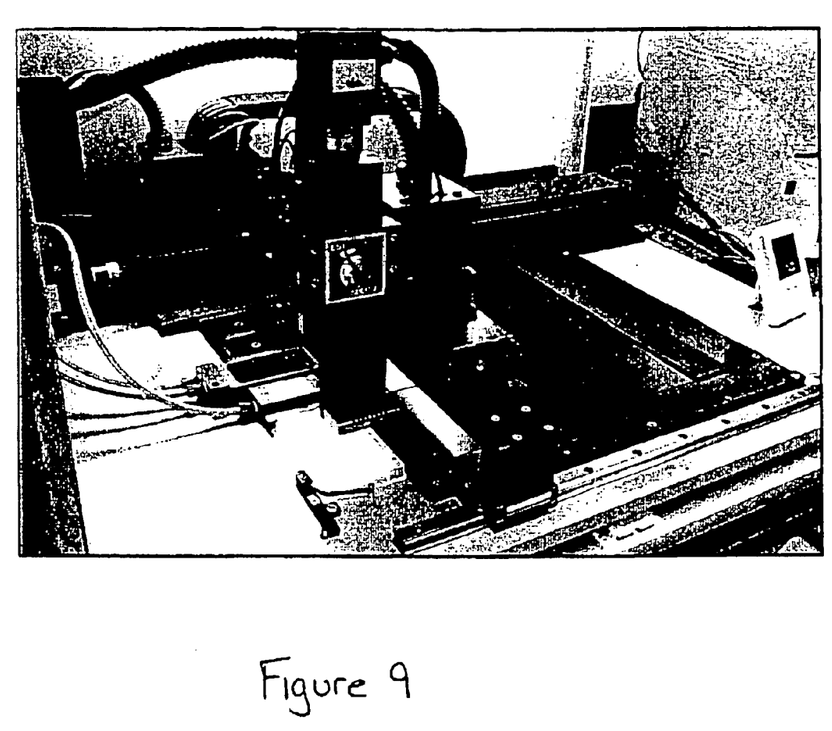
FIG. 9: A photograph of a complete microarray device.

The present invention is directed to systems and methods for producing microarrays using an improved slide platform and vacuum manifold, and variable pin contact velocity. FIG. 9 shows a view of a preferred microarrayer. The invention may be used with any suitable microarrayer, such as the SDDC-2 microarrayer (The Microarray Centre; Princess Margaret Hospital/Ontario Cancer Institute, Toronto, Canada; Virtek Vision International Inc. and Engineering Services Inc.).

Vacuum Manifold

Figure 4:
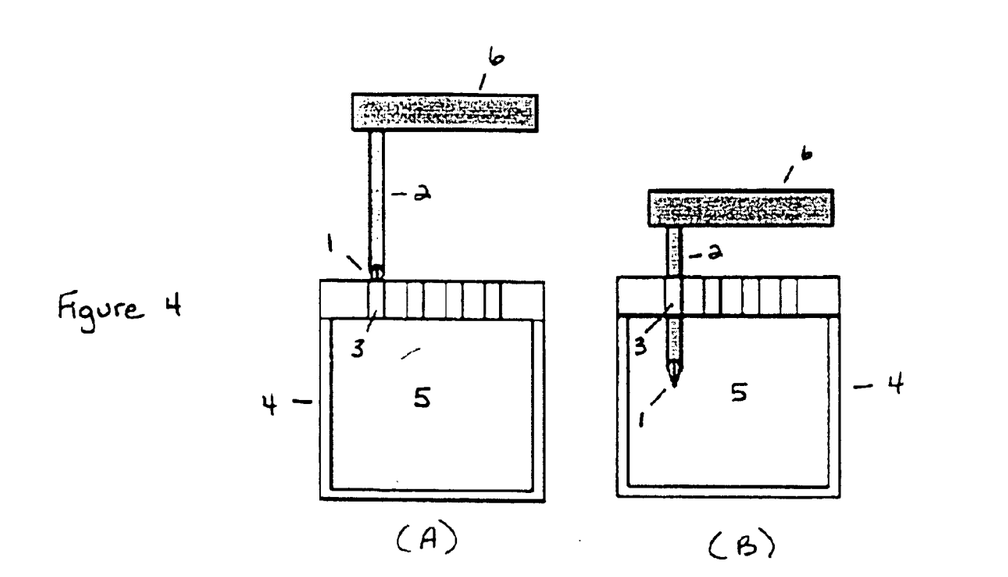
FIG. 4(A): Side view of a vacuum manifold with the pins set such that the tips were at the opening of the hole. In this way increased air flow is able to pass over the pin helping to draw off any liquid.
FIG. 4(B): Side view of an alternative vacuum manifold which allows the tips of the pins to pass completely into the chamber. The pins almost seal the chamber allowing the vacuum to pull the liquid off of the pin.
Figure 5:
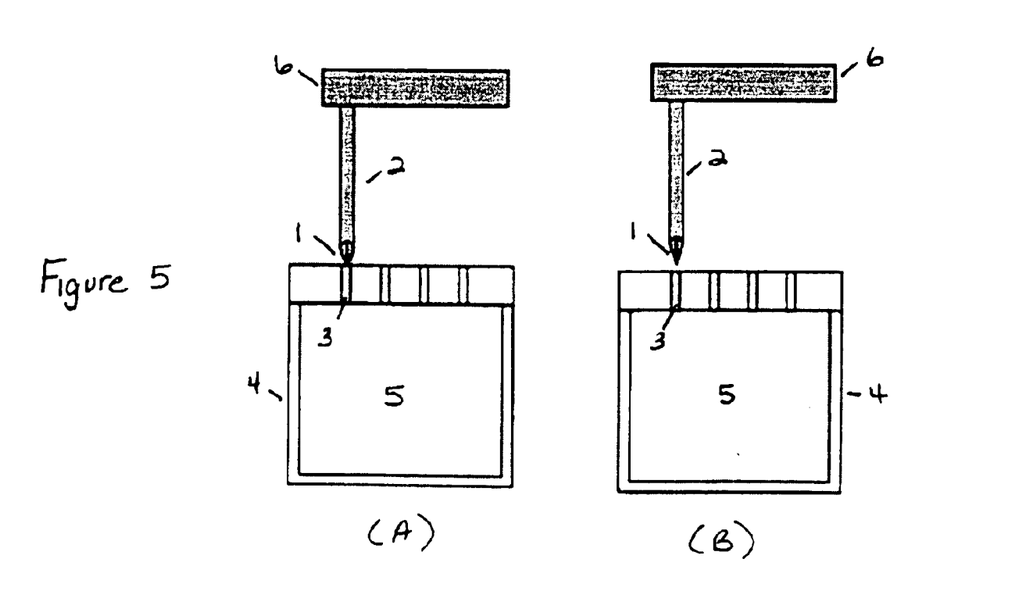
Figure 6:
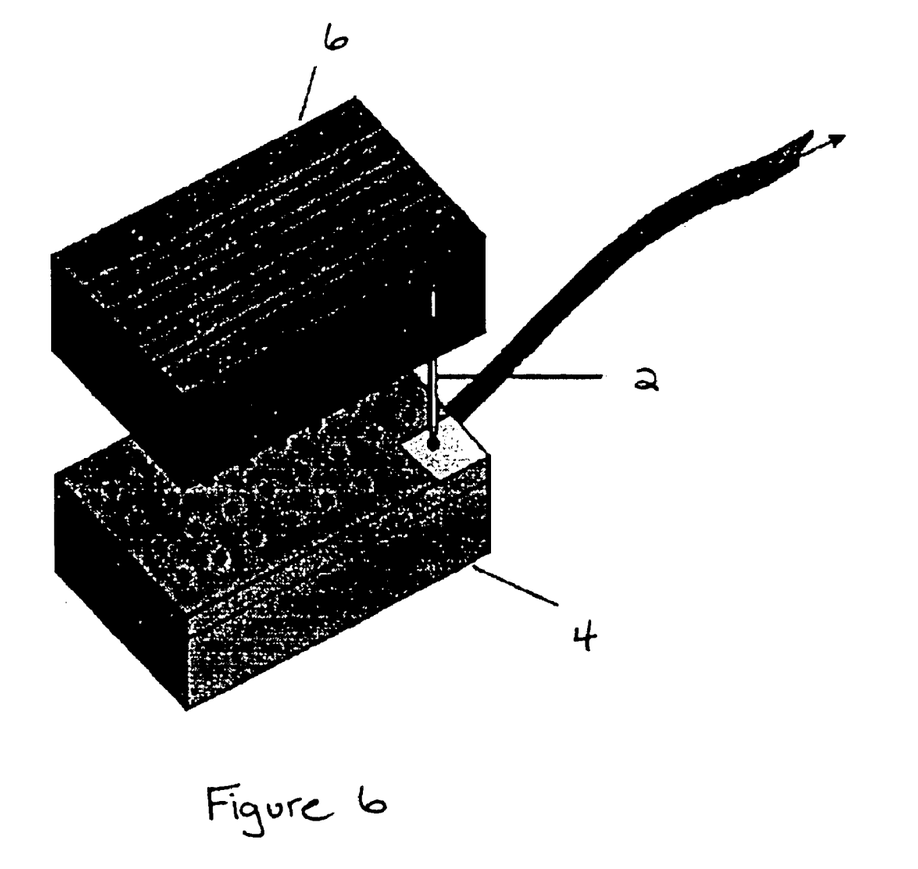
FIG. 6: A manifold including a gasketed chamber, with a series of 32 holes at the same spacing as the pins. When not all of the holes were in use, a piece of adhesive foil could be used to cover the unused holes thus increasing airflow.

One embodiment of the present invention (see FIGS. 4(A), 5, and 6) relates to a vacuum manifold 4 for removing liquid from microarray spotting members 2 after spotting, preferably comprising a plate with channels or holes 3 drilled in the plate, the holes leading to a chamber 5 which is connected to a source of vacuum. Each spotting member 2 is placed in or near a hole on the plate; liquid on the spotting members, typically a cleaning solution, is drawn away by the pressure created by the vacuum. As a result the spotting member 2 is cleaned after spotting. Preferably, the channels or holes 3 are arranged in parallel rows, in the same fashion the spotting members are arranged on the printing head.

The spotting members 2 are preferably pins, of either the solid or split types. Some commercially available pins include Telechem Chipmaker 2 pins, Telechem Chipmaker 3 pins. A combination of the two may also be used as the spotting members of a microarrayer.

Figure 1:
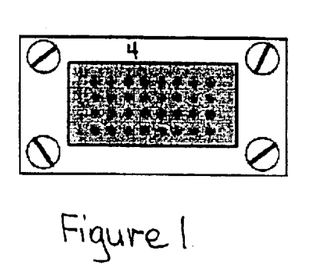
FIG. 1: A top plan view of an embodiment of the vacuum manifold that includes placing a piece of material, such as adhesive aluminium foil, over the manifold. Smaller holes (micro apertures) may be created, for example, by using either an off-spec spotting pin or a 28 gauge needle. The holes preferably have an approximate diameter of 1/32 of an inch for Telechem Chipmaker 2 or 3 pin but are variable according to the size of the pins.
Figure 2:
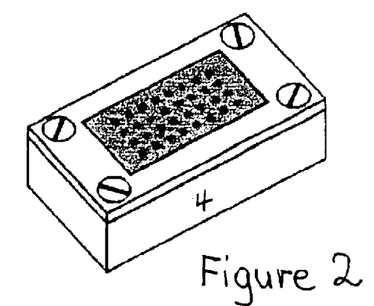
FIG. 2: A perspective view showing the side, top, and front of the embodiment shown in FIG. 1.
Figure 3:
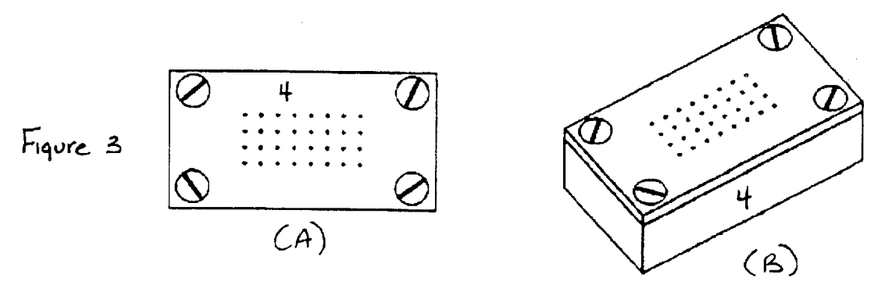
FIG. 3(A): A top plan view of a second embodiment of the invention which includes a manifold into which the holes that were machined had approximately 1/32 of an inch diameter. This avoids the need to use the adhesive foil, which is prone to wear over time.
FIG. 3(B): A perspective view showing the side, top, and front of the embodiment shown in FIG. 3(A).

Significantly improved cleaning is achieved by using this vacuum manifold 4. First, the inlets (holes/apertures) of the vacuum manifold are reduced in cross-sectional area. Alternatively, the inlets may be effectively reduced by placing a piece of sticky aluminum foil over the manifold and making new holes with a 28 gauge needle, or with an off-spec spotting pin (FIG. 2). Alternatively, the manifold could be constructed with smaller apertures 3 (FIG. 2). The magnitude of reduction of the cross-sectional area is preferably such that only a portion (for example, approximately half) of the pin tip 1 could fit through the aperture 3 and the pin body 2 cannot enter the aperture. Secondly, the pins 2 are preferably set to be about 100 micrometers above the manifold. From this point the pins 2 are reciprocated up and down to create further air turbulence, which result in excellent cleaning (3 to 5 percent carryover at maximum).

Slide Platform

Figure 7:
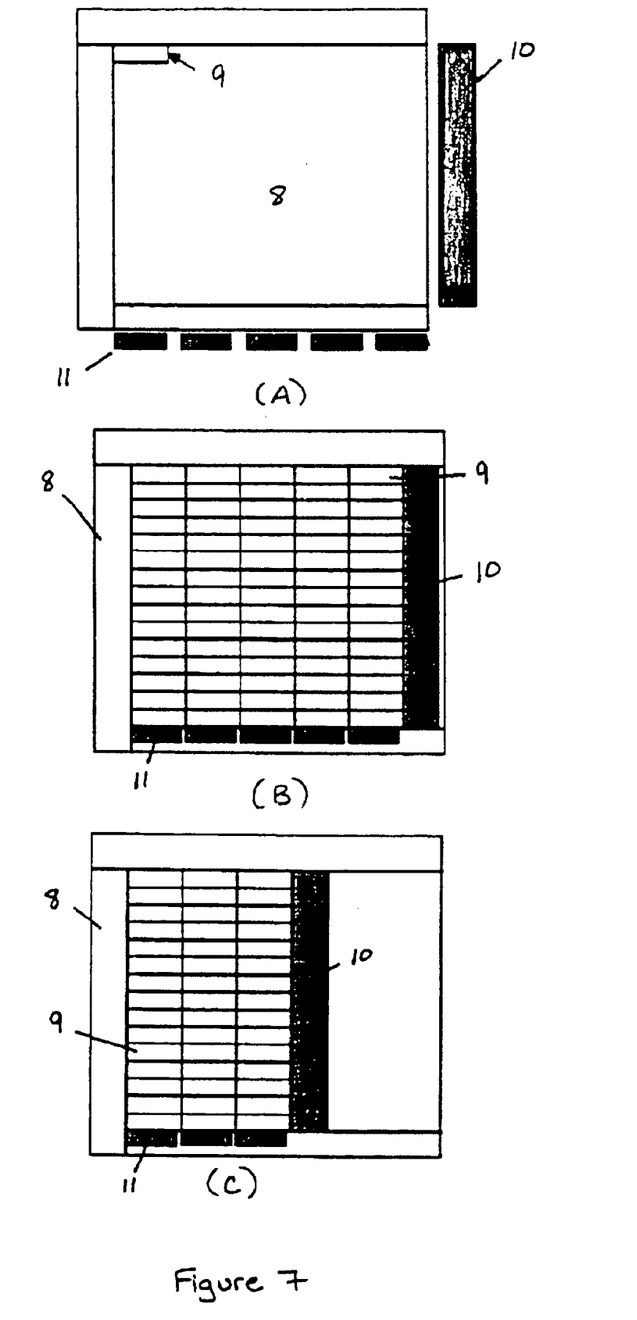
Figure 8:
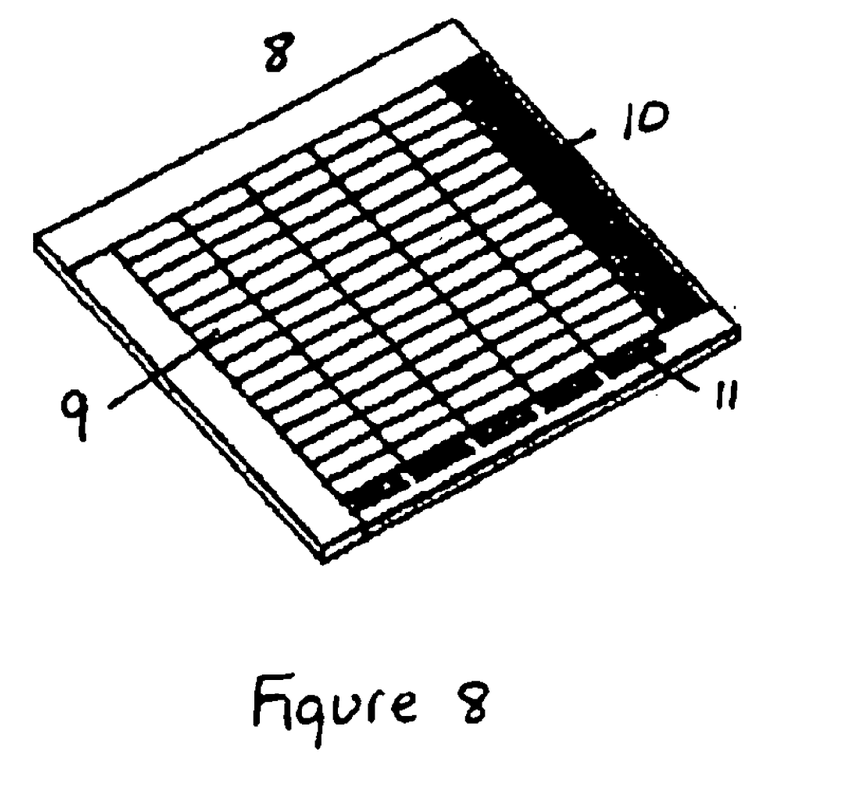
FIG. 8: A perspective view of the slide holder with a full complement of slides. All of the end bars and the heavy steel bar are used to hold the slides securely in place.

One embodiment of the present invention relates to a support device for holding microarray substrates in place during microarrayer operation, comprising a flat platform 8 on which the substrates are placed, the flat platform including an array surface including a first bar on one peripheral edge; a second bar on a second peripheral edge perpendicular to the first bar; a third bar on a third peripheral edge perpendicular to the second bar and opposed to the first bar, the third bar capable of applying force to the substrates to hold them in place during microarray operation; and a plurality of end bars perpendicular to the first and third bars and opposed to the second bar, the end bars capable of being located on the fourth peripheral edge or on the array surface spaced apart from the fourth peripheral edge, the end bars capable of applying force to the substrates to hold them in place during microarray operation.

The flat slide platform 8 is preferably less than 200 micrometer variation from one corner to the other. This design allows for the use of any size of slide 9, thus providing extreme flexibility. (See FIGS. 7 and 8 for details of one variation.) There is no limitation to the use of either imperial or metric 1×3 inch slides 9, but can, if required, use larger slides or smaller slides 9 (1×1 inch, 2×3 inch or any other size, both custom and standard stock). Loading and unloading of the platform 8 is also extremely easy to perform on a flat platform 8 because we simply place the slides 9 on the surface and slide them into position. This allows extremely quick loading of the arrayer, and results in overall efficiency.

A heavy bar 10 is preferably used to push up against the sides in one axis to hold the slides 9 in place. This helps to ensure that vibration from the arrayer does not cause the slides 9 to move in the x-y plane. In addition it helps to make sure the slides 9 are not bumped out of place when a technician is accessing the arrayer. End bars 11, which are preferably small bars around the length of a standard microscope slide 9 are preferably used to hold the slides 9 in place in the second axis. In this case, several of these "unit-sized" bars 11 could be used depending on the number of slides 9 on the platform 8. Magnets 11 are preferably used for these small bars, as this would provide a downward force to hold these bars in place. The platform 8 itself is preferably constructed of aluminium. Aluminum is preferred due to the precision with which it can be machined and the lightness of the material. To allow for the magnets 11 to work, a ferromagnetic bar, plate or sheet, typically steel in construction, is preferably added to the bottom or edge of the platform 8.

Blotting

One embodiment of this invention concerns a blotting device for blotting liquid from the exterior of microarray spotting members, comprising a blotting surface for drawing liquid from the microarray spotting members when the microarray spotting members contact the blotting surface; and structure for contacting the microarray spotting members with the blotting surface. One variation involves a glass surface.

Another aspect of the embodiment includes a processing system for directing the microarray spotting members to make more than one contact with the blotting surface in a predetermined pattern so that no portion of the blotting surface is contacted by more than one microarray spotting member. The processing system preferably includes a software-driven system.

During a typical run both blot slides and plates containing probe material, are preferably removed and replaced simultaneously. It is advantageous to replace blot slides concomitantly with probe plates. Plates containing probes elements typically possess 384 wells. If each sample is blotted 10 times, the software and blotting slides must accommodate 3840 spots with each spot separated by sufficient distance.

Two objectives are fulfilled during the blotting process. First, a sufficient number of spots are produced on the blots to remove excess material from the pins that may yield large spots on the array; and secondly, successive rounds of blotting (with material loaded onto pins at the beginning of each spotting cycle) must not overlap previous spots.

These two criteria translate into two basic motions that occur during the process of printing on the blot slides. In one direction (x), a series of spots is produced to remove excess material from the pins. Prior to the printing of each new set of probes the pins preferably move in a perpendicular direction (y) before printing the next series of blotting spots. The number of iterations required in each direction is determined empirically. This is accomplished by examining the size and morphology of spots produced by a set of pins. A centre to centre distance of approximately 0.5 mm for adjacent spots is sufficient. Blotting protocols can be modified to allow for greater distances.

The criteria described above and for a centre to centre distance of 0.5 mm, appropriate and sufficient blotting can be fulfilled if the following parameters are adopted. In both the x and y directions, the distances (in millimeters) the pins move between blots is preferably equal to the half number of pins in the direction of motion. For a single pin (one pin in x and one pin in y), the distance traversed between spots (x direction) and in the y direction (after each cycle of printing) is preferably 1 divided by 2 mm. For 4 pins in the y direction and 1 pin the x direction (4 pins total). The required motions for sufficient spacing of blot spots is approximately 2 mm and 0.5 mm respectively. Twelve print cycles are preferably required when using 32 pins (8 pins in the x and 4 pins in the y direction), to spot all probe samples in a single 384 plate. The required distances in the x and y direction over the blot slides are preferably 2 mm in the y direction and 4 mm in the x direction. As demonstrated above the basic principles are sufficiently flexible to accommodate a variety of pin configurations.

Adhering to these conditions will help ensure the synthesis of well-ordered and well-configured microarrays.

Variable Pin Contact Velocity

Robotic fabrication of microarrays requires several changes of joint velocity in order to provide the best quality of printing. There are three critical points at which velocity should to be changed: during printing onto the slides 9, during pin 2 blotting, and during the loading of the pins 2 with the biological probe sample.

Velocity Change During Printing onto the Slides

During printing onto the slides 9 it is necessary to both approach and depart from the slides 9 at a relatively slow speed in order to promote optimal spot quality. If the pins 2 approach the slide 9 too quickly they will create "micro splashes" which will disrupt spot morphology. Similarly, if the pins 2 are pulled away from the slide 9 too quickly, then the spots can be pulled in such a way that morphology is disrupted. The following exemplary aspects were determined:

1) Due to the floating architecture of certain preferred pins, the pins may be moved past the point of the initial touch with the substrate, typically glass, without damaging the tips: they simply lift out of the print head slightly. The "down position", otherwise known as the second position, for the pins on the slides should be set such that these are moving approximately 200 micrometers, as an example, past the point at which contact is made between the tip and the glass. Setting the down position in this way does two things. The first is that it provides a more gentle touch onto the slide, and the second is that it in effect allows for a dwell time in which the pins remain in contact with the slides. In other words, the pins come in contact with the slide, and remain in contact while the print head continues downward for about 200 micrometers, and as it returns up away from the slide.

2) The "up position", otherwise known as the first position, for the pins over the slides should be approximately 2 millimeters, as an example, above the value selected for the "down position". This ensures that there is proper clearance above the platform such that during lateral movement the pins will not hit anything causing them damage.

3) The robot is set with an overall "safe position" which is significantly high above the platform to allow any gross movements without collision. This distance is often about 50 mm or more above the platform.

4) During printing the robot will travel from this "safe position" to the "up position" at the user-selected velocity for all gross movements.

5) As a spot is made, the robot performs the movement from the "up position" to the "down position" (hereafter referred to as the printing movement) via a timed, "velocity independent" movement. Regardless of the user-selected velocity for gross movements, the printing movement is done at a timed speed. Studies have found that a rate of about 1 mm per 50 to 100 milliseconds was appropriate. As such, the approximately 2 mm printing movement is set to take about 100 to 200 milliseconds to complete. Similarly the departure movement as the pins move away from the slide back to the "up position", also takes about 100 to 200 milliseconds to complete.

As an example of how the robot may be programmed for printing onto the chips using timed Z-axis movements, the first instruction of a piece of code commands the robot to move in the z-axis only to a calibrated point from its current position. The robot is preferably instructed to perform this movement in about 100 milliseconds. The next two instructions output the robot's current position as determined by the encoders as well as the desired position of the robot in the x-axis (for monitoring precision). The fourth instruction moves the robot back up in the z-axis to another calibrated point, preferably also in 100 milliseconds. At this point the robot again displays the actual and desired y-axis positions of the robot for monitoring precision.

This procedure leads to ideal spot morphology with one particular set up (3×SSC spotting solution, DNA concentration of 0.1 to 0.2 micrograms/microliter), however differing spotting solutions and DNA concentrations require different timings due to changes in viscosity. To a person in the art, it is clear that variations to the mentioned parameters may also be used for proper performance, for example the extent that the pins are allowed to drop past touching the slide (approximately 200 micrometers in this case), the height of the pins in the "up position" (about 2 mm above the "down position"), and the duration the pin rests on the slide. These numbers are offered as examples. Lower viscosity solutions are likely to splash more easily but will make larger spots. As a result it is generally preferred that (1) the approach speed be reduced; (2) the distance past touching be reduced; and (3) the departure speed be reduced. Typically higher viscosity solutions will have (1) the distance past touching increased to increase dwell time; or (2) an additional step to provide a dwell time of defined duration after touching. With higher viscosity solutions approach and departure speeds can be increased which will compensate for the required dwell time.

Velocity Changes During Blotting

It is important that deposition of probe DNA yield regularly spaced spots of uniform morphology. Not all deposition or spotting pins designed to the same specifications behave in a similar manner. Each will load an amount characteristic of the pin. Consequently, the size of the first spots produced from a set of pins will be significantly variable. The greatest concern is that deposition of excessive material on the microarrays may yield overlapping spots. The results of which will effect contamination of the material spotted on the arrays as well as the material in the probe plates. As spotting proceeds the excess material is removed and the size of spots become uniform. The purpose of the blot slide or blot pad is to remove the excess material from the pins prior to the spotting on to the microarray slides. This has helped ensure the production of well order arrays with uniform spot configuration.

The Blot slides are preferably composed of polished glass or similar material. High-quality microscope slides work very well. To maximize the space allocated to the printing of arrays, it is important to determine the minimum size required for the Blot Slide to perform adequately. Sufficient distances are allowed between spotted material to preclude the possibility of overlapping of spots. A centre to centre distance of about 0.5 mm (millimeter) is optimal. Sufficient numbers of spots are printed to ensure uniformity of spots to be subsequently printed on to the arrays.

Typically, all the parameters for blotting a pin on a blot slide are the same as for printing on a slide, although slightly faster velocities can be used, such as at about 75–100 milliseconds, to travel the typically 2 mm distance from the pin up position (the first position) to the down position (the second position).

A robot blotting routine using timed Z-axis movements preferably involve a first step loading a counter with the number of blots to be performed. The second step sets up a loop which is to be executed the number of times by the counter. The first step of the loop moves the robot down in the z-axis to a calibrated position from its current position in preferably 100 milliseconds. The next step moves the robot back up in the z-axis to another calibrated point in preferably 100 milliseconds. After this movement, the robot is instructed to move laterally (for example, parallel to the x-axis) a set distance between two blots. This movement is set to take about 200 milliseconds to avoid abrupt movement of the robot. In a subsequent step the robot finishes its lateral movement before proceeding on to the next step. The robot then moves back up to a safe position.

To a person in the art, it is clear that variations to the above mentioned parameters may also be used for proper performance of the microarray microarrayer. The above parametric values are offered as examples. Again, lower viscosity solutions are likely to splash more easily but will make larger spots. As a result it is generally preferred that (1) the approach speed be reduced; (2) the distance past touching be reduced; and (3) the departure speed be reduced. Typically higher viscosity solutions will have either (1) the distance past touching increased to increase dwell time; or (2) an additional step to provide a dwell time of defined duration after touching. With higher viscosity solutions approach and departure speeds can be increased which will compensate for the required dwell time.

Velocity Changes During Loading of the Pins

Loading of the pins 2 involves dipping the pins into the solution, which is to be printed. This solution is contained within the "well" of a multi-well source plate. Each pin 2 dips into a discrete well. When using multi-well plates that have relatively large diameter wells, such as those found in a 96-well plate (diameter is 6 mm), loading of the pins 2 is relatively simple. The pins 2 can be dipped into the solution within the well and withdrawn with relatively quick movements. However optimal loading appears to be a function of velocity for these plates. When using source plates with a smaller diameter well opening, like in a 384-well plate (diameter is typically 3 mm), loading becomes even more velocity dependent. When using plates such as these, the pins 2 must be more carefully positioned in the well. In addition, the solution in the well is more prone to stick to the sides of the plates. Quick movements of the pin 2 in and out of the well will cause the solution to be "splashed" or "dragged" up the sides of the well, which can in fact overload the pins 2. Pin overloading (i.e. solution is present on the outside of the pin where it should not be) will lead to sample wastage as well as decreased spot uniformity.

The following are examples of ways to use changes in velocity to ensure optimal pin 2 loading:

1) The pins should be lowered into the source plate slowly in a timed movement. This lowering is done at a rate independent of the user-selected velocity for gross movements of the robot.
2) The pins should also be withdrawn from the source plate using a slow timed movement such that the solution is allowed to drain off of the pins rather than being dragged up on the pin.
3) Normally the plates are calibrated to have two vertical (z-axis) positions, the first being the up position outside of the well and the second being the down position inside of the well. The addition of an extra calibration point(s) leads to added ability to change velocity during loading.
4) Although the following uses 3 z-axis calibration points, but this methodology could be extended to include any additional calibration points:
   a. The first calibration point is the "safe position" of the robot. This position is the same for all points of the robot and is a position high enough over the base of the robot such that the pins cannot collide with any objects.
   b. The second calibration point is the "up position" (also known as the first position) which is set such that the tips of the pins are just outside of the wells of the source plate.
   c. The third calibration point is the "down position" (the down position). This position is selected to be the point at which the pins are just touching the bottom of the wells (or perhaps a little past the point of touching).

5) The velocities are preferably controlled in the following way:
   a. Movement from the safe position to the up position (the first position) is performed at the user-selected velocity. This is a gross movement and does not need to be slowed down. Slowing down such a large movement would only serve to waste valuable time.
   b. Movement from the up position to the down position is timed. Depending on the depth of the well, this time may change. With the 384-well source plates, this distance is covered in approximately one second (the overall rate then is about 12–15 millimeters per second).
   c. Movement out of the well from the down position to the up position is also timed and with one typical set up takes 1 second (again a rate of about 12–15 mm per second)]. The up position is typically about 12 to 15 mm away from the down position and the movement is set to take approximately 1 second.
   d. The final movement from the up position back to the safe position is performed again at the user-selected velocity to maximize efficiency.

These timings are again variable according due to the set up and the viscosity of the solution. Again we are using 3×SSC and 0.1 to 0.2 micrograms per microliter DNA concentrations. To a person in the art, it is clear that variations to the mentioned parameters may also be used for proper performance of the microarrayer. These numbers are offered as examples. Lower viscosity solutions are likely to splash more easily but will make larger spots. As a result it is generally required that (1) the approach speed be reduced; (2) the distance past touching be reduced; and (3) the departure speed be reduced. Higher viscosity solutions will require that either (1) the distance past touching be increased to increase dwell time, or (2) an additional command be added to provide a dwell time of defined duration after touching. With higher viscosity solutions approach and departure speeds can be increased which will compensate for the required dwell time.

The robot may be programmed for loading of the pins 2 with biological material which first directs the robot to move to a calibrated position (the up position) which is just above the source plate. This movement is carried out at the user-selected or default velocity. The following step instructs the robot to wait until movement is finished before proceeding onto the next command. The third step involves the robot moving down in the z-axis to the calibrated position (the down position), which is a point at which the pins touch the bottom of the well. This movement is set to take, as an example, about 1000 milliseconds (1 second). Again the robot is instructed to wait until movement is finished before proceeding. At this point the robot is instructed to move back up to the up position coordinate at which point the pins are out of the source plate. Again this movement is to take, as an example, 1000 milliseconds. After the movement is finished, the robot moves back up to the safe position using the user-selected or default velocity.

It will be appreciated that the above description relates to the preferred embodiments by way of example only. Many variations on the apparatus for delivering the invention will be obvious to those knowledgeable in the field, and such obvious variations are within the scope of the invention as described and claimed, whether or not expressly described.

All patents (including U.S. Pat. No. 6,084,373), patent applications, and publications referred to in this application are incorporated by reference in their entirety.

We claim:

1. The manifold assembly for removing liquid from in combination, a plurality of microarray spotting members, and a plurality of microarray spotting members, the spotting members each having a spotting member body and a first open end portion for printing a spot on a microarray slide, comprising:

a plate, the plate defining a plurality of fluid flow apertures extending through the plate, each aperture located to cooperate with a corresponding spotting member, each aperture having an axis a first diameter, an upstream edge forming an inlet and a downstream edge forming an outlet, the edges defining the aperture, the corresponding spotting member body having a second diameter wherein the second diameter is greater than the first diameter so that the spotting member may not entirely pass through the aperture, and wherein the first open end portion of the spotting member is adapted to extend into the corresponding aperture to a position where there is space between the spotting member and the aperture; and turbulence means for creating turbulence in air flowing from the inlet to the outlet in the space between the spotting member and the aperture for removing liquid from the first open end portions of the spotting members.

2. The assembly of claim 1, wherein the turbulence means comprises i) aligning means for aligning the spotting members proximate to the apertures with each spotting member body extending generally axially away from the corresponding aperture, ii) reciprocating means for repeatedly reciprocating the spotting members generally axially toward and away from the apertures while maintaining the spotting members axially aligned with the corresponding apertures and limiting axially inward travel to provide clearance with the apertures in the limiting position and iii) vacuum means for drawing air around the spotting members to flow from the inlet to the outlet.

3. The assembly of claim 2, wherein the vacuum means comprises a source of vacuum and a structure for coupling the apertures to communicate with the source of vacuum to draw air around the spotting members to flow from the inlet to the outlet.

4. The assembly of claim 1, wherein the apertures comprise channels, the channels defined by the upstream and downstream edges.

5. The assembly of claim 4, wherein the apertures are arranged in parallel rows.

6. The assembly of claim 1 or 2, wherein the spotting members comprise pins.

7. The assembly of claim 6, wherein the pins are selected from the group consisting of solid pins and split pins.

8. The assembly of claim 1, comprising 48 apertures capable of simultaneously removing liquid from 48 spotting members.

9. The assembly of claim 1, comprising 32 apertures capable of simultaneously removing liquid from 32 spotting members.

10. The assembly of claim 4, further comprising a cover secured parallel to the plate over the inlets, the cover defining a plurality of cover apertures therethrough, each cover aperture concentric with an inlet of the plate, and the diameter of each cover aperture being less than the diameter of its concentric inlet.

11. The assembly of claim 1 or 2, wherein the first open end portion is tapered.

12. The assembly of claim 11, wherein approximately half of the tapered first open end portion is adapted to extend into the aperture.

13. The assembly of claim 2, wherein the first open end portion comprises a tip and the spotting member is reciprocable by the reciprocating means between first and limiting positions, the tip located outside the aperture in the first position and the tip located inside the aperture in the limiting position.

14. The assembly of claim 3, wherein the source of vacuum pressure provides a pressure of 50 to 90 psi.

15. The assembly of claim 3, wherein the source of vacuum pressure provides a pressure of 60 psi.

16. A microarrayer, said microarrayer comprising:
   a) a manifold assembly for removing liquid from a plurality of microarray spotting members;
   b) a plurality of spotting members each having a spotting member body and a first open end portion for printing a spot on a microarray slide;
   c) a plate, the plate defining a plurality of fluid flow apertures extending through the plate, each aperture located to cooperate with a corresponding spotting member, each aperture having an axis, a first diameter, an upstream edge forming an inlet and a downstream edge forming an outlet, the edges defining the aperture, a corresponding spotting member body having a second diameter wherein the second diameter is greater than the first diameter so that the spotting member may not entirely pass through the aperture, and wherein the first open end portion of the spotting member is adapted to extend into the corresponding aperture to a position where there is space between the spotting member and the aperture; and
   d) turbulence means for creating turbulence in air flowing from the inlet to the outlet in the space between the spotting member and the aperture for removing liquid from the first open end portions of the spotting members.

17. The microarrayer of claim 16, wherein the turbulence means comprises i) aligning means for aligning the spotting members proximate to the apertures with each spotting member body extending generally axially away from the corresponding aperture, ii) reciprocating means for repeatedly reciprocating the spotting members generally axially toward and away from the apertures while maintaining the spotting members axially aligned with the corresponding apertures and limiting axially inward travel to provide clearance with the apertures in the limiting position and iii) vacuum means for drawing air around the spotting members to flow from the inlet to the outlet.

18. A method of removing liquid from a plurality of microarray spotting members, comprising creating turbulence in air flowing from the inlet to the outlet of the assembly of claim 1 or the microarrayer of claim 16 in the space between the spotting member and the aperture for removing liquid from the first open end portions of the spotting members wherein turbulence is created in air by: applying a source of vacuum to the spotting members of the assembly to draw air around the spotting members to flow from the inlet to the outlet, aligning the spotting members proximate to the apertures with each spotting member body extending generally axially away from the corresponding aperture, repeatedly reciprocating the microarray spotting members generally axially toward and away from the apertures and limiting axially inward travel to provide clearance with the aperture in the limiting position to create turbulence in air flowing from the inlet to the outlet in the space between the spotting member an the aperture for removing liquid from the first open end portions of the spotting members.

19. The method of claim 18, wherein the spotting members are about 100 micrometers away from the inlet prior to reciprocation.

20. The method of claim 19, wherein the spotting members are reciprocated about a distance of 1 mm.

21. The method of claim 18, wherein each spotting member includes a tapered first open end portion adapted to extend into the aperture, the tapered first open end portion received in the aperture during at least part of the reciprocation.

22. The method of claim 21, wherein the first tapered open end portion reciprocates in and out of the aperture.

23. The method of claim 21, wherein the tapered first open end portion is spaced apart from the aperture during reciprocation.

24. A method of removing liquid from a plurality of microarray spotting members, the spotting members each having a spotting member body and a first open end portion for printing a spot on a microarray slide, the liquid removed through a plate, the plate defining a plurality of fluid flow apertures extending through the plate, each aperture located to cooperate with a corresponding spotting member, each aperture having an axis, a first diameter, an upstream edge forming an inlet and a downstream edge forming an outlet, the edges defining a corresponding aperture, a corresponding spotting member body having a second diameter wherein the second diameter is greater than the first diameter so that the spotting member may not entirely pass through the aperture, and wherein the first open end portion of the spotting member is adapted to extend into the corresponding aperture to a position where there is space between the spotting member and the aperture, the method comprising:
   first aligning the spotting members proximate to the apertures with each spotting member body extending generally axially away from the corresponding aperture;
   drawing air around the spotting members to flow from the inlet to the outlet; and
   repeatedly reciprocating the spotting members generally toward and away from the corresponding apertures while maintaining the spotting members axially aligned with corresponding apertures and limiting axially inward travel to provide clearance with the apertures in the limiting position,
   wherein turbulence is created in air flowing from the inlet to the outlet in the space between the spotting member and the aperture wall for removing liquid from the first open ends of the spotting members through the apertures.

25. The method of claim 24, wherein the spotting member is reciprocated between first limiting positions; the tip outside the aperture in the first position and the tip inside the aperture in the limiting position.

* * * * *